US006555367B1

United States Patent
Spence et al.

(10) Patent No.: US 6,555,367 B1
(45) Date of Patent: Apr. 29, 2003

(54) COMPLEX OF BIOTINYLATED VIRAL VECTOR AND LIGAND FOR TARGETED GENE DELIVERY

(75) Inventors: Sally E. Spence, Frederick, MD (US); Jeffrey S. Smith, Bethesda, MD (US); Jonathan R. Keller, Frederick, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/509,698
(22) PCT Filed: Oct. 9, 1998
(86) PCT No.: PCT/US98/21364
  § 371 (c)(1),
  (2), (4) Date: Jun. 15, 2000
(87) PCT Pub. No.: WO99/19500
  PCT Pub. Date: Apr. 22, 1999

Related U.S. Application Data

(60) Provisional application No. 60/061,587, filed on Oct. 7, 1997.

(51) Int. Cl.[7] .................. C12N 15/00; C12N 15/09; C12N 15/63; C12N 15/70; C12N 15/74
(52) U.S. Cl. .................. 435/320.1; 424/93.2; 424/93.6
(58) Field of Search ................... 424/93.2, 93.6; 435/320.1, 455

(56) References Cited

U.S. PATENT DOCUMENTS 5,547,932 A * 8/1996 Curiel et al. .................. 435/65

FOREIGN PATENT DOCUMENTS

| EP | 0 779 365 A2 | 6/1997 |
|---|---|---|
| WO | WO 97/05266 | 2/1997 |
| WO | WO 97/38723 | 10/1997 |

OTHER PUBLICATIONS

Miller N. and Vile R. "Targeted vectors for gene therapy"; The FASEB Journal 9: 190–199 (1995).*
Deonarain M. "Ligand–targeted receptro–mediated vectors for gene delivery"; Exp. Opin. Ther. Patents 8(1):53–69 (1998).*
Verma I. and Somia N. "Gene Therapy–promises, problembs and prospects"; Nature 389:239–242 (1997).*
Crystal R. "Transfer of Genes to Huamns: Early lessons and obstacles to success"; Science 270:4040–410 (1995).*
Reynold P. and Curiel D. "Strategies to adapt adenoviral vectors for gene therapy applciations:Targeting and Integration"; pp. 111–130 in Development of Human Gene Therapy Ed.Friedmann T. CSH press(1999).*
Chen S. et al. "Gene Therapy for brain tumors: Regression of experimental gliomas by adenovirus–mediated gene transfer in vivo"; Proc. Natl. Acad. Sci. USA 91(8): 3054–3057),(1994).*
Link H. et al. "Combined tansplantation of allogeneic bone marrow and CD34+ blood cells"; Blood, 86(7): 2500–2508 (1995).*
Goodman S. et al. " Recombinant adeno–associated virus mediated gene trasnfer into hematopoietic progenitor cells"; Blood 84(5): 1492–500, ((1994).*
Schwarzenberger et al."Targeted Gene Transfer to Human Hematopoietic Progenitor Cell Lines Through the C–Kit Receptor" Abstract No. 96141066 *Blood* 87(2):472–478, Jan. 15, 1996.
Willheim et al. "Purification of Human Basophils and Mast Cells Multistep Separation Technique and mAb to CDw17 and CD117/c–kit" *J. Immunol. Methods* 182:115–129, 1995.
Mayer et al. "De–novo Expression of CD44 and Survival in Gastric Cancer" *The Lancet* 342:1019–1022, Oct. 23, 1993.
Roux et al. "A Versatile and Potentially General Approach to the Targeting of Specific Cell Types by Retroviruses: Application to the Infection of Human Cells by Means of Major Histocompatibility Complex Class I and Class II Antigens by Mouse Ecotropic Murine Leukemia Virus–Derived Viruses" *Proc. of the Natl. Acad. of Sci. of the USA,* 86(23):9079–9083, Dec. 1989.

* cited by examiner

*Primary Examiner*—Scott D. Priebe
*Assistant Examiner*—Peter Paras, Jr.
(74) *Attorney, Agent, or Firm*—Needle & Rosenberg, PC

(57) ABSTRACT

The present invention provides a composition for targeted delivery of a nucleic acid to a cell comprising a biotinylated recombinant adenovirus, wherein biotin is covalently linked to the recombinant adenovirus, wherein the recombinant adenovirus comprises the nucleic acid, and wherein the recombinant adenovirus is linked via streptavidin to a biotinylated targeting moiety. Also provided by this invention is a method for targeted delivery of a nucleic acid to a selected cell in a subject comprising administering to the subject a composition comprising a biotinylated recombinant adenovirus, wherein biotin is covalently linked to the recombinant adenovirus, wherein the recombinant adenovirus comprises the nucleic acid, and wherein the recombinant virus is linked via streptavidin to a biotinylated targeting moiety that specifically targets the selected cell.

20 Claims, 10 Drawing Sheets

COMPLEX OF BIOTINYLATED VIRAL VECTOR AND LIGAND FOR TARGETED GENE DELIVERY

This application claims priority to U.S. Provisional Application Serial No. 60/061,587, filed Oct. 7, 1997, and PCT /US8/21364 filed on Oct. 9, 1998.

BACKGROUND OF THE INVENTION

1. Field of the Invention

The present invention is in the field of targeted gene delivery. Specifically, the invention relates to recombinant viral vectors for targeted delivery to selected cells, wherein the recombinant virus is a small, encapsidated virus, such as adenovirus or adeno-associated virus.

2. Background Art

Recent attempts to target gene transfer to human cells have focused on the use of retroviral and adenoviral vectors. However, the most promising current vectors have resulted in limited success, due in part to the inability to target specific cell types such as hematopoietic stem cells, and the need to culture target cells in vitro to promote cell cycling which can result in the loss of stem cell function. The ability to target gene transfer to specific cell types in situ would greatly enhance current approaches to gene therapy.

Several approaches have been taken to target viral and non viral vectors that include using ligands, antibodies or peptides in the vector construction thereby redirecting virus infection through antigens or receptors expressed on specific cell types. Early experiments designed to redirect the host range of retroviruses by molecular modification of ecotropic envelopes to recognize cellular receptors through antigen binding, ligand or peptide sequences were unsuccessful. It has subsequently been shown that efficient uncoating of the virus requires a conformational change in a subunit of the envelope protein which is only induced upon interaction of the retrovirus particle with its cognate receptor; thus retroviruses directed to alternate receptors do not yield high frequencies of infection.

Similarly, the use of bifunctional antibodies which recognize both viral epitopes and target cell antigens to redirect the tropism of amphotropic retroviruses have not resulted in targeted gene transfer. Successful targeting of retroviruses has required construction of chimeric amphotropic envelopes which contain a protease cleavage site and a targeting moiety. Following recognition of the target cell by the targeting moiety, proteases cleave the chimeric sequences to leave the intact amphotropic envelope. Because the virus is now in close proximity to the cell surface, the viral envelope can interact with its authentic receptor and viral infection will proceed.

The present invention utilizes the biology of adenovirus infections to confer several advantages to the use of recombinant adenoviruses for targeted gene transfer. Infection of a cell by adenovirus requires two distinct receptors, one for recognition and one to mediate internalization of the virus. First, the knob portion of the capsid fiber interacts with a recently identified receptor on the cell surface, then internalization of the adenovirus is mediated by interaction of the penton base protein with integrins (fibronectin and vitronectin) on the cell surface. The adenovirus capsid uncoats in the acidic endosome (i.e., does not require interaction with a receptor to mediate a conformational switch) and the DNA is delivered to the nuclear pore.

It has been demonstrated that targeting of adenoviruses can be accomplished by redirection of host range by linkage to bispecific antibodies. Several groups have also reported that molecular modifications to introduce chimeric viral proteins have met with success. However, bispecific antibodies limit the usefulness of targeted vectors for in situ gene transfer due to the effects of serum on antigen-antibody interactions, and introduction of sequences encoding chimeric viral proteins into the viral genome can adversely affect virus function. Therefore, there is a need for more efficient, effective, specifically targeted adenoviral vectors that retain their infectivity characteristics for gene delivery for a variety of purposes.

The present invention fills this need by providing a vector, and particularly an adenoviral vector, that can be linked to any selected targeting moiety for targeting to any selected cell type. The vector is highly efficient, achieving high levels of expression of the transferred gene specifically in the targeted cells, The present invention provides a vector wherein biotin is covalently linked to recombinant adenovirus particles such that through an avidin bridge we could redirect the virus using biotinylated growth factors and antibodies.

Targeted gene transfer to specific populations of hematopoietic progenitor cells represents an advance towards therapeutic use of gene transfer. The c-kit receptor has been shown to be expressed on the surface of primitive hematopoietic cells with long term reconstitution activity, and represents an attractive receptor for targeted gene transfer. Therefore, a molecular conjugate vector consisting of plasmid DNA encoding the luciferase reporter gene complexed with polylysine coupled to avidin (for addition of the biotinylated ligand) and defective adenovirus particles was used to target hematopoietic progenitors (*Blood* 87:472–478, 1996). Upon the addition of biotinylated steel factor (SLF) we demonstrated that this vector specifically targets c-kit+hematopoietic cell lines and results in up to a ten fold increase in luciferase activity as compared to a control vector. Furthermore, transient gene expression is observed with maximum expression at 30 hours, and greater than 90% of target cells are transfected. However, the potential for use of this vector for in vivo gene transfer is limited by the inclusion of polylysine in the molecular conjugate for two reasons: 1) polylysine yields a high background due to non-specific electrostatic interactions with the cell surface, 2) the electrostatic charges required to hold the molecular conjugate vector together may be rapidly neutralized in the presence of human serum. Other laboratories have approached targeted gene transfer by modifying the tropism of recombinant adenoviral vectors through a neutralizing anti-fiber antibody chemically conjugated to cell-specific ligands (*Nature Biotechnology* 14:1574–1578, 1996). These vectors represent an improvement over the molecular conjugate vector in that the targeting moiety is no longer attached to the vector through electrostatic charges, resulting in a decrease in the non-specific background, but the affinity of the antibody-antigen interaction required for targeting of these vectors is variable and is not stable in the presence of serum. A third approach to targeted adenoviral vectors has been to molecularly clone sequences encoding the targeting moiety into the fiber or penton base structural genes of the adenoviral vector. This approach is expected to avoid the disadvantages of targeting through antibody-antigen interactions, but necessitates extensive manipulation of the adenoviral genome to introduce each targeting moiety.

The present invention provides more efficient vectors for gene transfer. The vectors were generated by direct high affinity linkage of the targeting moiety to a recombinant virus particle. To achieve these inventive vectors, the invention includes a protocol for the covalent addition of biotin to the capsid of recombinant encapsidated small virus particles. The present invention demonstrates that biotin can be linked to the capsid of recombinant adenovirus while maintaining wild-type infectivity. Following incubation with streptavidin, any biotinylated ligand or antibody could be added to target this vector to any cell type.

SUMMARY OF THE INVENTION

The present invention provides a composition for targeted delivery of a nucleic acid to a cell comprising a biotinylated recombinant encapsidated virus, wherein the recombinant virus comprises the nucleic acid to be delivered, and wherein the biotinylated recombinant virus is linked via streptavidin to a biotinylated targeting moiety.

The present invention specifically provides a composition for targeted delivery of a nucleic acid to a cell comprising a biotinylated recombinant adenovirus, wherein the recombinant adenovirus comprises the nucleic acid to be delivered, and wherein the biotinylated recombinant adenovirus is linked via streptavidin to a biotinylated targeting moiety.

The present invention further provides a method for targeted delivery of a nucleic acid to a selected cell in a subject comprising administering to the subject a composition comprising a biotinylated recombinant encapsidated virus comprising the nucleic acid to be delivered, wherein the virus is linked via streptavidin to a biotinylated targeting moiety that specifically targets the selected cell.

The present invention further provides a method for targeted delivery of a nucleic acid to a selected cell in a subject comprising administering to the subject a composition comprising a biotinylated recombinant adenovirus comprising the nucleic acid to be delivered, wherein the virus is linked via streptavidin to a biotinylated targeting moiety that specifically targets the selected cell.

No Ligand: Open bar: MO7e cells infected with biotinylated recombinant adenovirus.

Closed bar: MO7e cells infected with biotinylated recombinant adenovirus treated with avidin.

+Bio SCF: Open bar: MO7e cells treated with biotinylated recombinant adenovirus and 25 ng of biotinylated SCF in the absence of an avidin bridge.

Closed bar: MO7e cells treated with biotinylated recombinant adenovirus linked to 25 ng of biotinylated SCF through an avidin bridge.

+Bio CD34: Open bar: MO7e cells treated with biotinylated recombinant adenovirus and biotinylated anti-CD34 antibody in the absence of an avidin bridge.

Closed bar: MO7e cells treated with biotinylated recombinant adenovirus linked to biotinylated anti-CD34 antibody through an avidin bridge.

+Bio CD44: Open bar: MO7e cells treated with biotinylated recombinant adenovirus and biotinylated anti-CD44 antibody in the absence of an avidin bridge.

Closed bar: MO7e cells treated with biotinylated recombinant adenovirus linked to biotinylated anti-CD44 antibody through an avidin bridge.

+Bio CD117: Open bar: MO7e cells treated with biotinylated recombinant adenovirus and biotinylated anti-CD117 (anti-c-kit) antibody in the absence of an avidin bridge.

Closed bar: MO7e cells treated with biotinylated recombinant adenovirus linked to biotinylated anti-CD117 (anti-c-kit) antibody through an avidin bridge.

Figure 1:
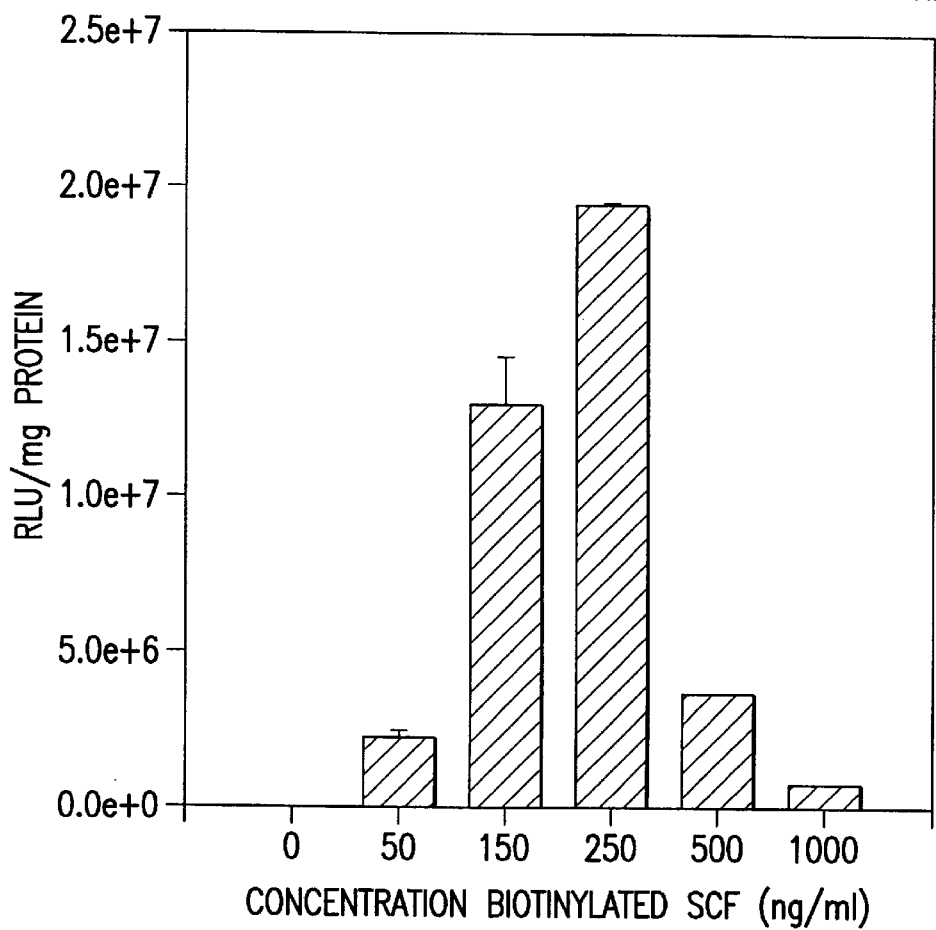
FIG. 1 shows the effects of concentration of biotinylated SLF on efficiency of targeted transfection by recombinant adenovirus. Hematopoietic cell lines were transfected with the SLF-targeted recombinant adenovirus encoding luciferase, and after 24 hours, harvested and luciferase gene expression measured. The graph depicts relative light units (RLU) per mg protein as concentration of SLF is increased from 0 to 1000 ng/ml, in c-kit⁻ cells. The data are presented as the mean RLU of duplicate determinations ± the SE and are representative of at least three experiments.
Figure 2:
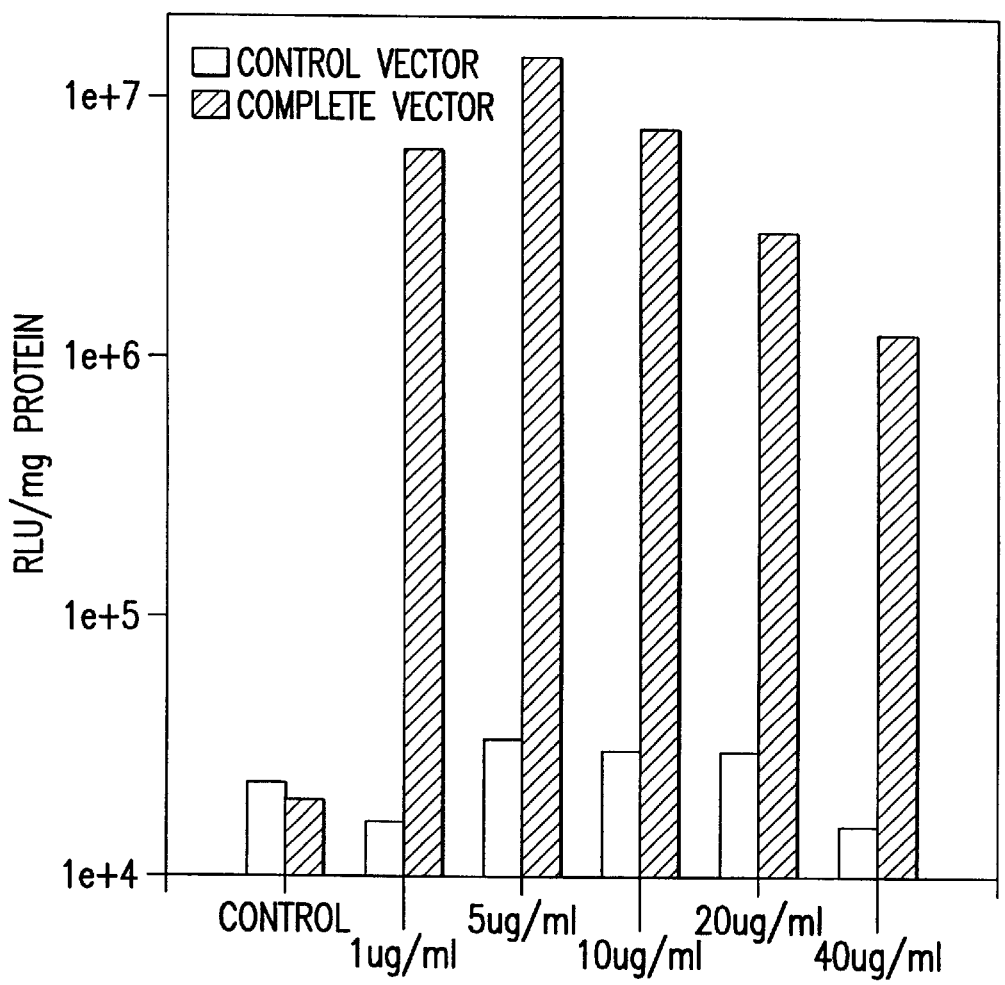
FIG. 2 shows the effects of concentration of neutravidin on targeted adenovirus transfection of MO7e cells. Cells were harvested after 48 hours. The graph shows the relative light units (RLU) per mg protein measured from MO7e cells upon transfection with steel factor-targeted recombinant adenovirus encoding luciferase, when various concentrations of neutravidin are used (from 0 to 40 µg/ml). The open bars represent control vector (nontargeted recombinant adenovirus: adenovirus vector linked to avidin without steel factor (complete vector lacking targeting moiety)), and the closed bars represent complete vector (with targeting moiety) of the present invention.
Figure 3:
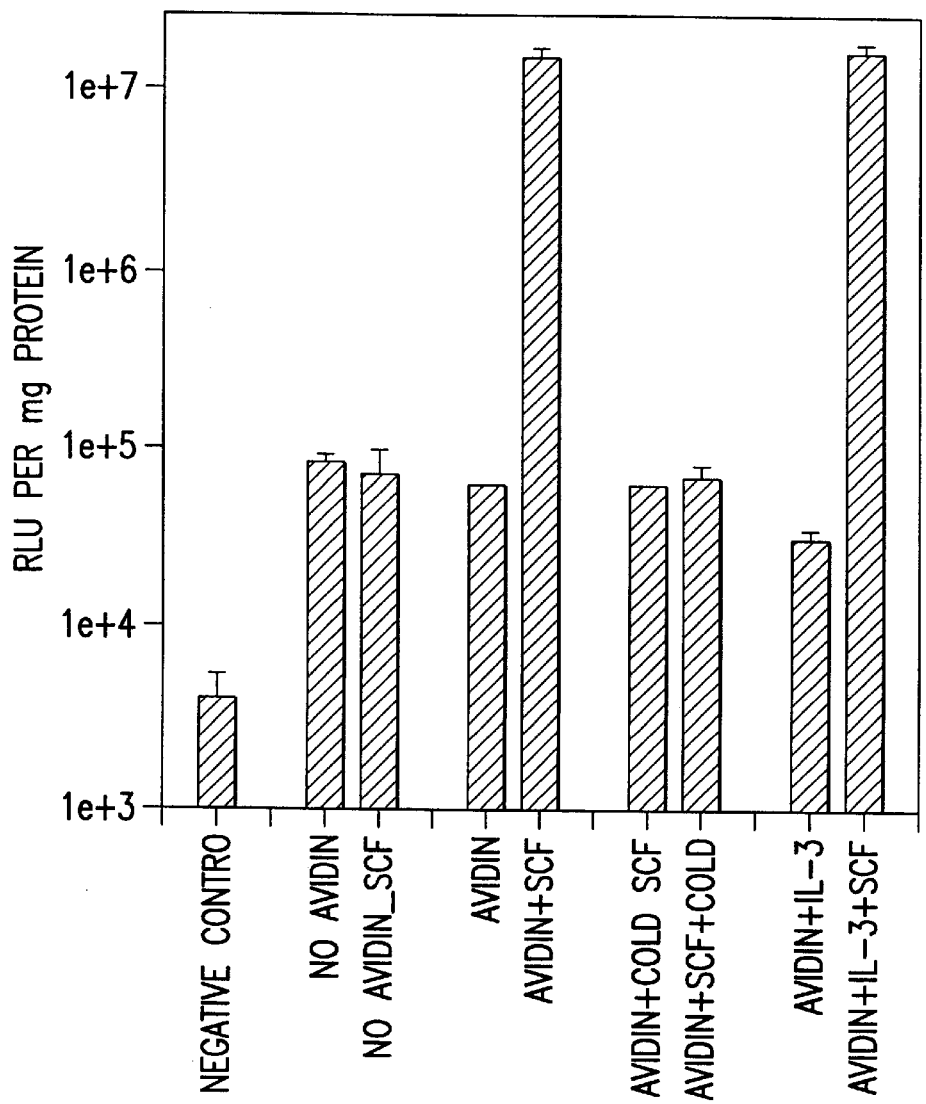
FIG. 3 shows the specificity of targeted adenovirus gene transfer to MO7e cells through the c-kit receptor. Cells were transfected with the recombinant adenovirus vector encoding luciferase having the targeting moieties as indicated, harvested after 24 hours, and luciferase gene expression in the cells measured. The graph depicts relative light units (RLU) per mg protein. The results indicate that SLF present but not linked to the adenovirus vector competed out the vector for targeting MO7e cells, and the addition of IL-3, an unrelated targeting moiety, did not compete for targeting MO7e cells. The first set of bars is the negative control which is untreated MO7e cells. The remaining bars are labeled as follows: No avidin: MO7e cells treated with biotinylated adenovirus in the absence of avidin and biotinylated SCF; No avidin+SCF: MO7e cells treated with biotinylated adenovirus and biotinylated SCF in the absence of avidin; Avidin: MO7e cells treated with biotinylated adenovirus linked to avidin in the absence of biotinylated SCF; Avidin+SCF: MO7e cells treated with biotinylated adenovirus linked to biotinylated SCF through an avidin bridge; Avidin+cold SCF: MO7e cells pretreated with 500 ng/ml SCF were subsequently infected with biotinylated adenovirus linked to avidin; Avidin+SCF+cold: MO7e cells pretreated with 500 ng/ml SCF were subsequently infected with biotinylated adenovirus linked to biotinylated SCF through an avidin bridge; Avidin+IL-3: MO7e cells pretreated with 500 ng/ml IL-3 were subsequently infected with biotinylated adenovirus linked to avidin; and Avidin+IL-3+SCF: MO7e cells pretreated with 500 ng/ml IL-3 were subsequently infected with biotinylated adenovirus linked to biotinylated SCF through an avidin bridge.
Figure 4:
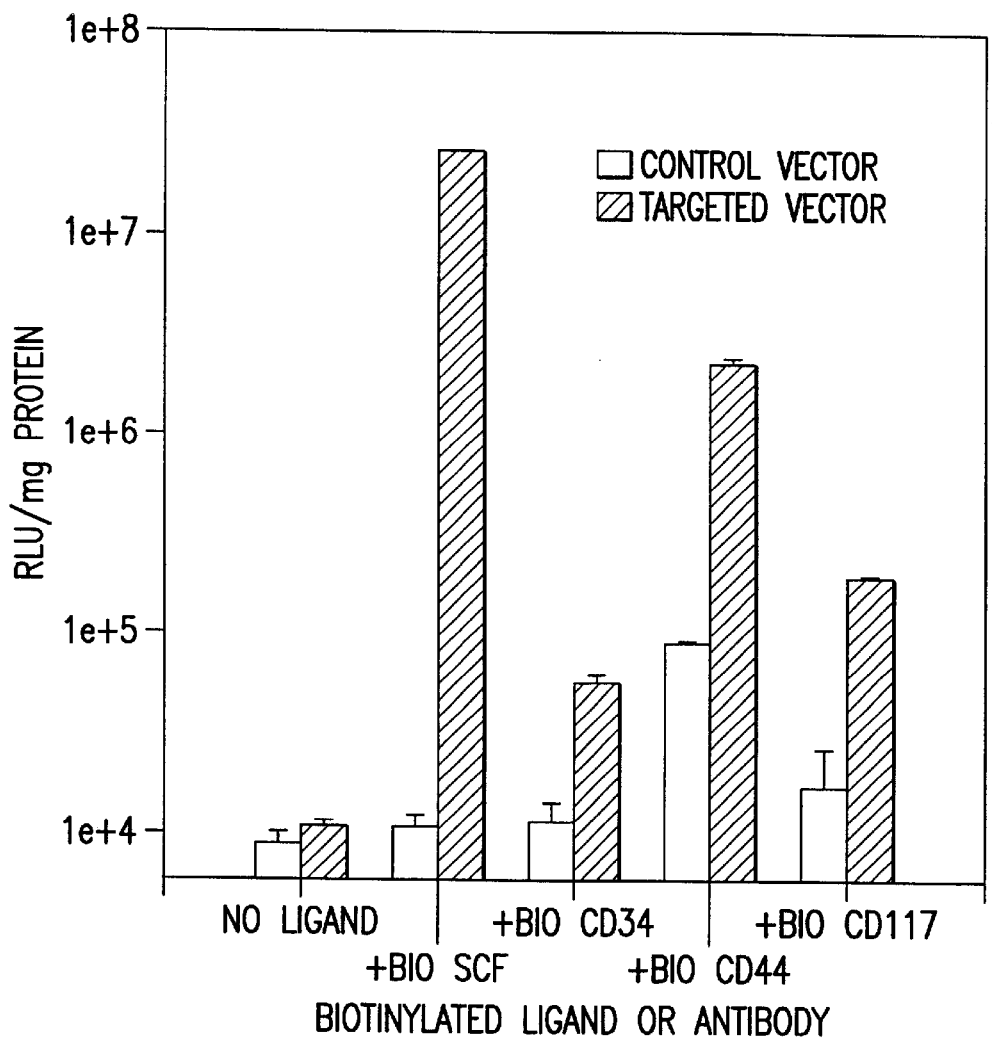
FIG. 4 shows the versatility of biotinylated recombinant adenovirus in targeting surface markers on MO7e cells. The open bars represent control vector, and the closed bars represent targeted vector. "Bio CD34", "Bio CD44", and "Bio CD117" represent recombinant adenovirus vector having as targeting moieties biotinylated antibodies to various cell surface markers present on MO7e cells to which SLF can bind. The graph shows transfection (RLU/mg protein) of MO7e cells with recombinant adenovirus vectors having the indicated targeting moiety linked via biotin-streptavidin linkage. The Y-axis is labeled as follows: 1e+4=$10^4$; 1e+5=$10^5$; 1e+6=$10^6$; 1e+7=$10^7$; 1e+X-axis is labeled as follows.
Figure 5:
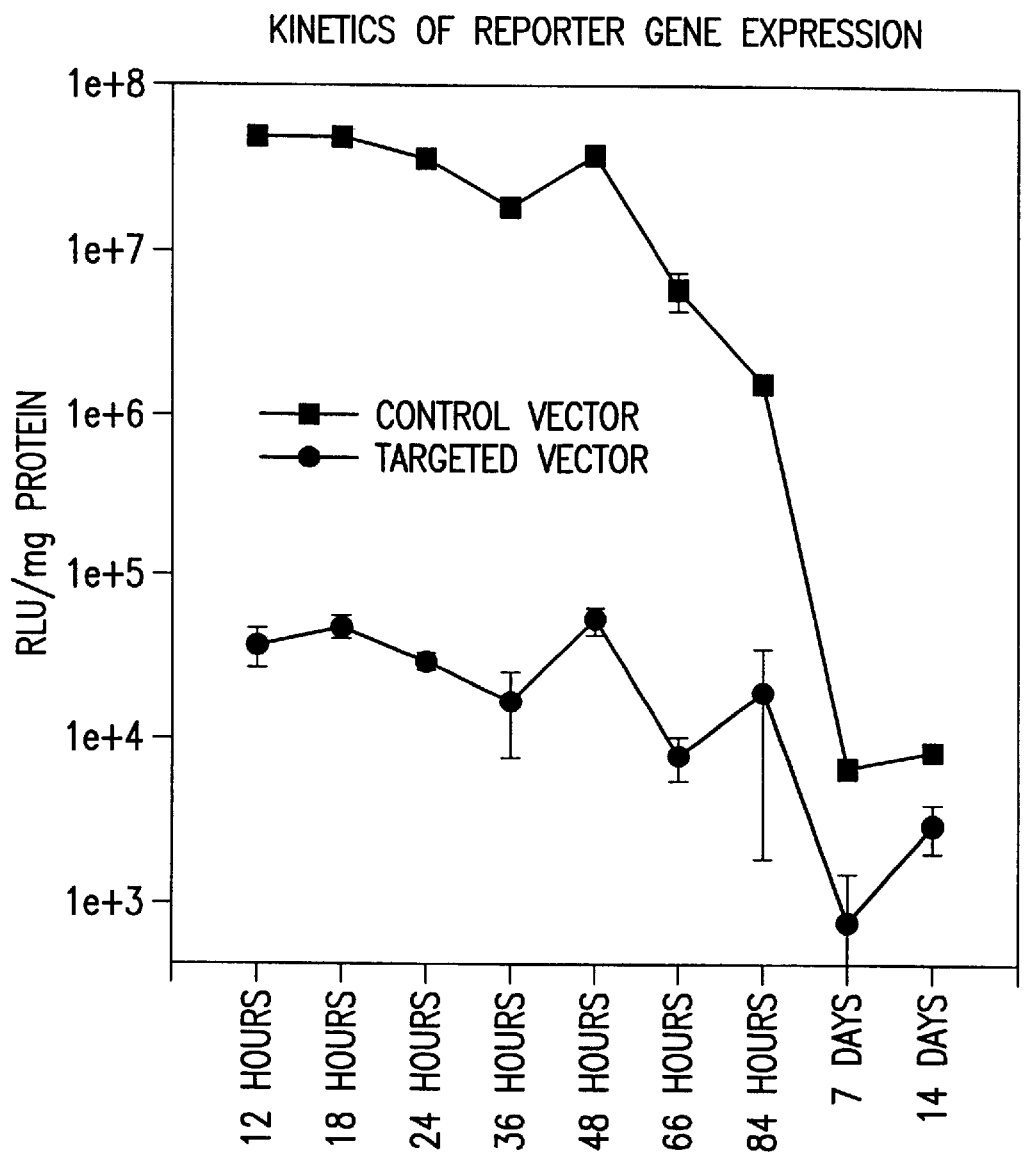

FIGS. 5 shows the kinetics of gene expression. The -•-indicates control vector and -■-indicates SLF-targeted recombinant adenovirus vector encoding luciferase. Expression of the luciferase gene is measured over 14 days (RLU/mg protein) following transfection.

Figure 6A:
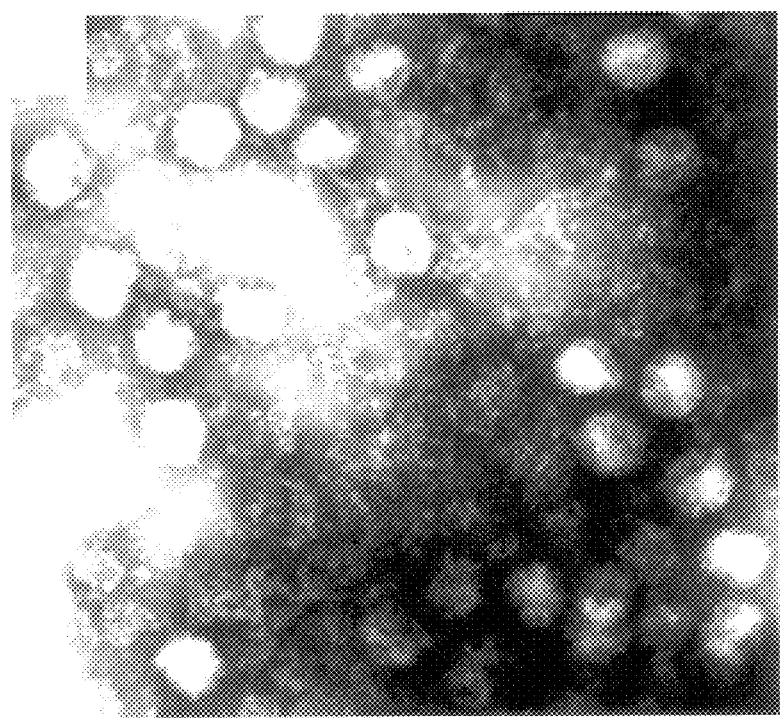
Figure 6B:
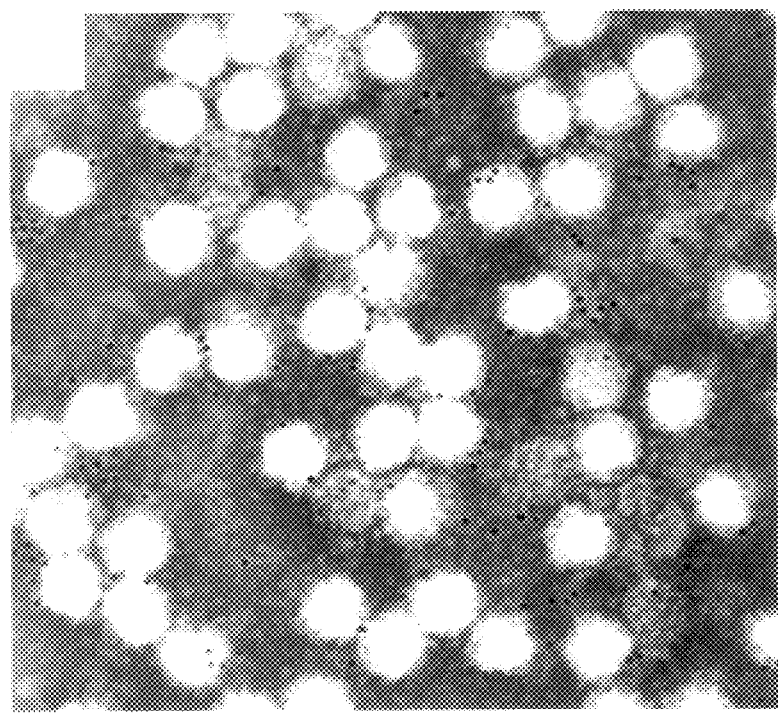

FIGS. 6 (A–B) shows electron micrographs of (A) control and (B) biotinylated recombinant adenovirus. Recombinant adenovirus AdCMVuc was incubated with 100 µg/mL photoactivatable biotin and irradiated at a wavelength of 350 nm for 5 minutes; control virus was treated identically except for addition of photoactivatable biotin. Following incubation With colloidal gold-streptavidin, negative stain immunoelectron microscopy was performed (17) and photographs were taken a magnification of 135,000.

Figure 7A:
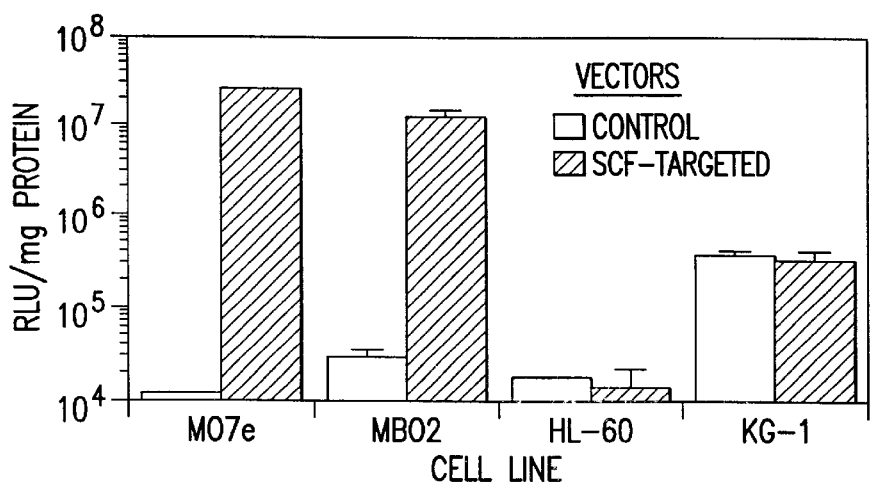
Figure 7B:
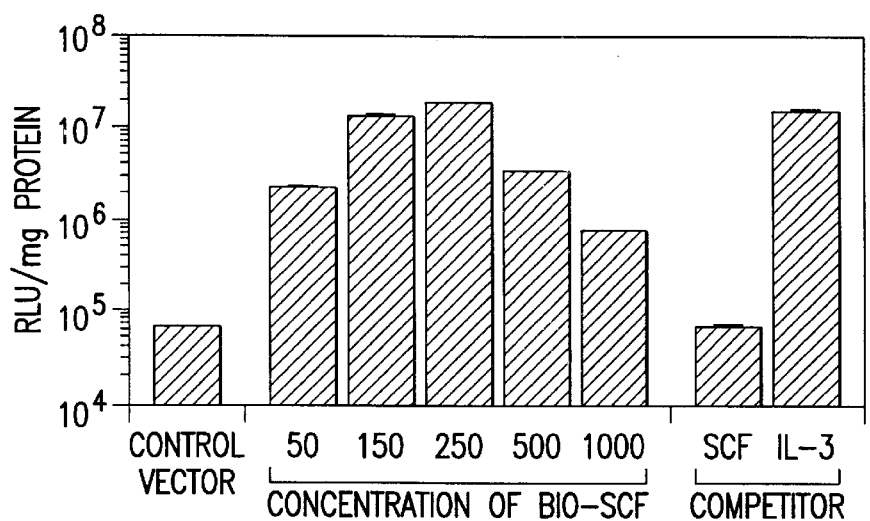
Figure 7C:
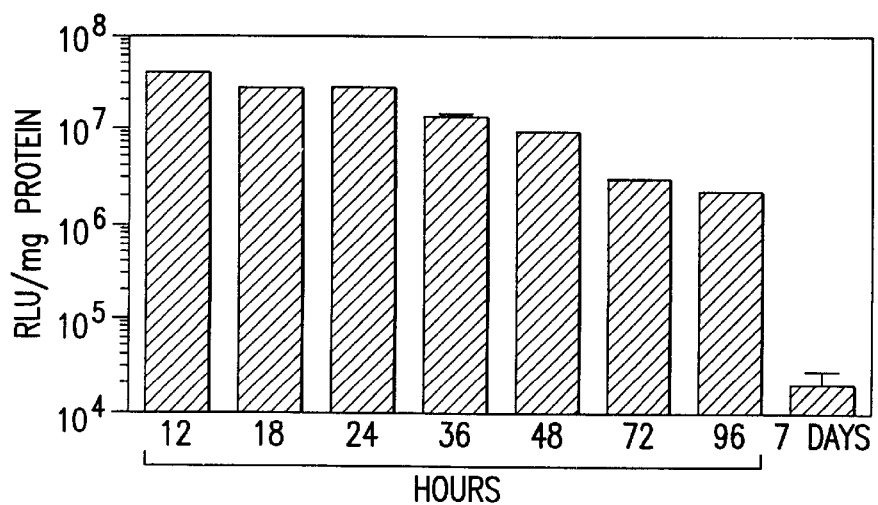

FIGS. 7 (A–C) shows (A) Infection of c-kit$^+$ and c-kit$^+$ cells by SCF-targeted recombinant adenovirus. Biotinylated recombinant adenovirus linked to avidin was incubated with either 250 ng/mL of SCF (control vector) or 250 ng/mL of bio-SCF (SCF-targeted vector) (18) prior to infection of the c-Kit$^+$ cell lines MO7e and MBO2 and the c-Kit$^+$ cell lines HL-60 and KG-1 (19). Twenty four hours after infection the luciferase activity was measured and reported as he average relative light units (RLU)/mg protein of two determinations±SE. The results are representative of two separate experiments. (B) Specificity of SCF-targeted gene transfer to MO7e cells. SCF-targeted vectors were constructed by incubating biotinylated virus linked to avidin with 50 to 1000 ng/mL of recombinant human bio-SCF. In competition experiments, the SCF-targeted vector was constructed by incubating biotinylated virus with 250 ng/mL of bio-SCF, and MO7e cells were incubated with 500 ng/mL non-biotinylated SCF or IL-3 prior to infection with 100 µL the SCF-targeted vector. (C) Kinetics of luciferase gene expression following infection of MO7e cells with SCF-targeted vectors. SCF-targeted vectors were constructed by adding 250 ng/mL to biotinylated virus linked to avidin. At various times following infection, MO7e cells were harvested and assayed for luciferase expression. At all time points, luciferase activity of cells infected with the control vector was less than $2 \times 10^4$ RLU/mg protein.

Figure 8A:
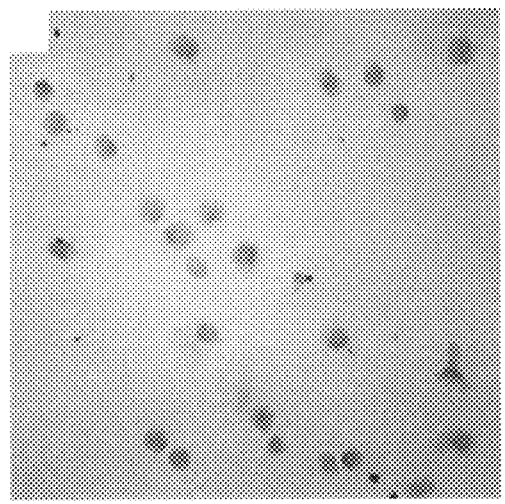
Figure 8B:
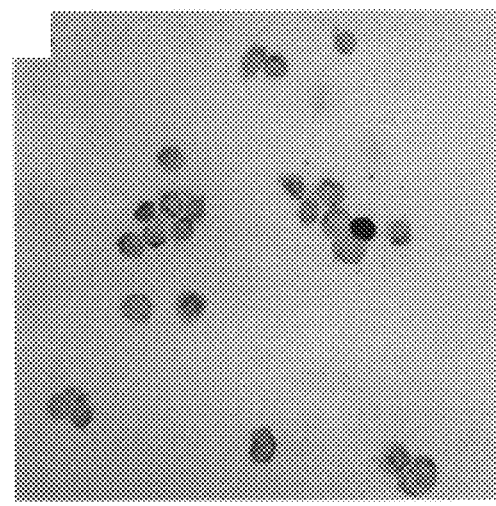
Figure 8C:
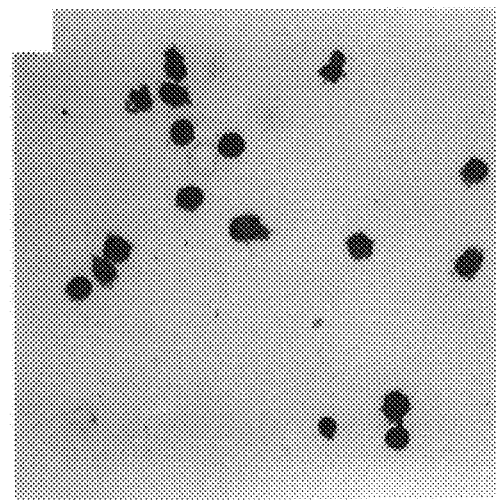

FIGS. 8 (A–C) shows frequency of SCF-targeted infection of MO7e cells. MO7e cells were either (A) untreated, (B) treated with 100 µL of biotinylated virus, or (C) treated with 100 µL of the SCF-targeted vector constructed with 250 ng/mL of bio-SCF. Twenty four hours later, cells were harvested and in situ PCR specific for amplification of luciferase DNA was performed. Photographs were taken at 1000×magnification on a Leitz Laborlux D Wild MPS 46 microscope, and are representative of 500 cells per slide scored on duplicate slides from three separate experiments.

Figure 9A:
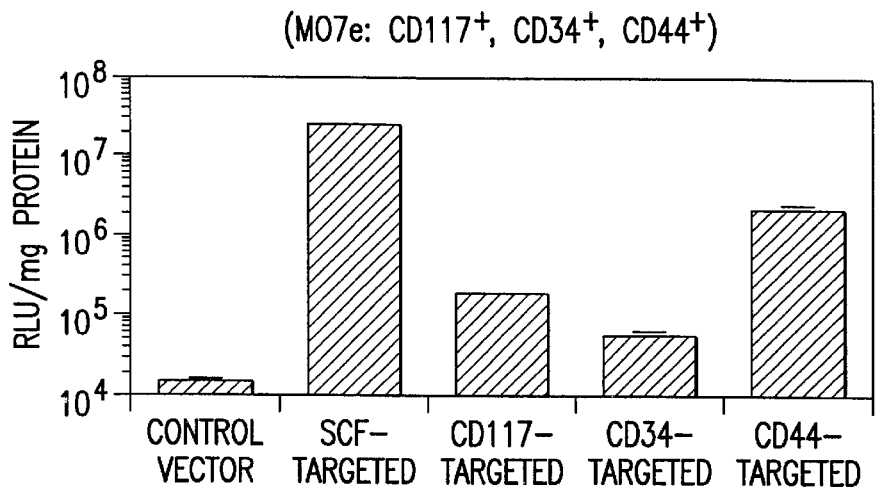
Figure 9B:
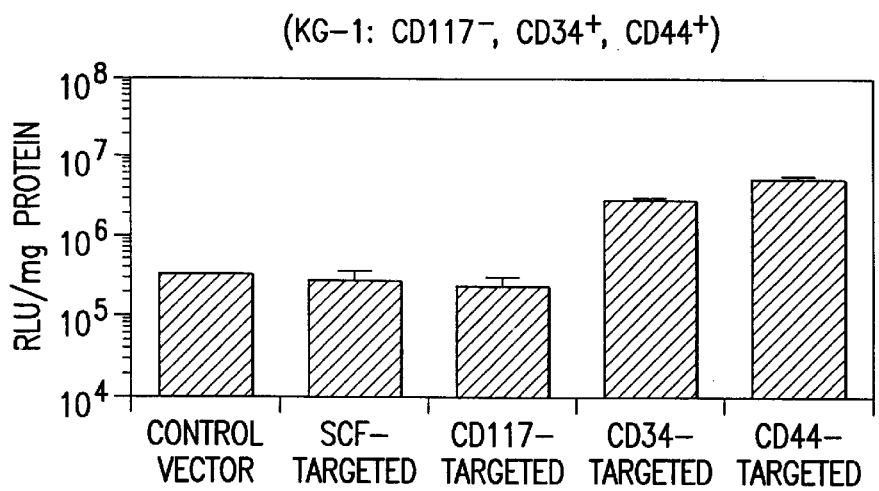
Figure 9C:
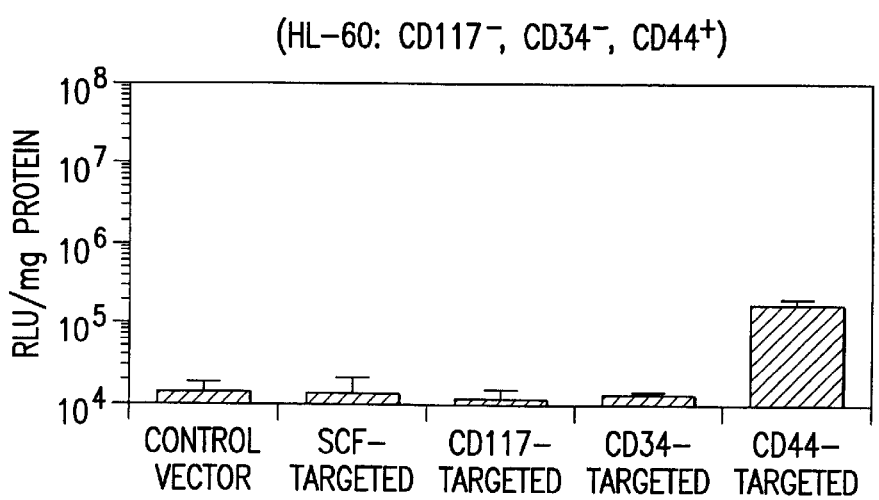

FIGS. 9 (A–C) shows targeting of hematopoietic cell lines with biotinylated recombinant adenovirus linked to antibodies. (A) The c-kit$^+$, CD34$^+$, CD44$^+$ cell line MO7e was infected with 100 µL of biotinylated recombinant adenovirus lined to avidin (control), 250 ng/mL biotinylated SCF (SCF-targeted), 20 µg/mL biotinylated anti-CD117 (antibody to c-kit, CD117-targeted), 20 µg/mL biotinylated anti-CDer-targeted) or 2.5. µg/mL biotinylated anti-CD44 antibodies (CD44-targeted). The (B) c-kit$^+$, CD34$^+$, CD44$^+$ KG-1 cells and (C) c-kit$^+$, CD34$^+$, CD44$^+$ HL-60 cells were treated identically to MO7e cells. Luciferase activity at 24 hours after infection is reported as the mean ±SE of duplicate determinations and is representative of two experiments.

Figure 10:
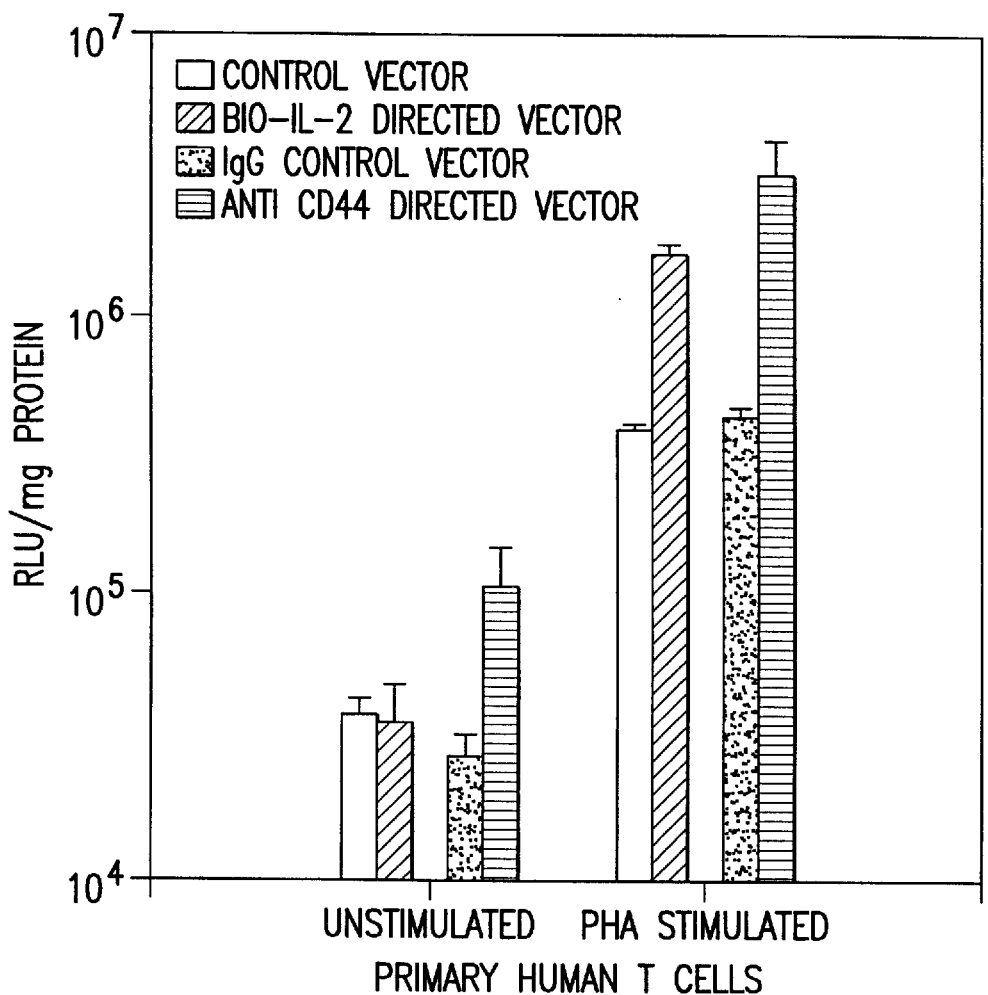

FIG. 10 shows the successful gene transfer to primary human T cells using IL-2 and CD44 directed virus.

DETAILED DESCRIPTION OF THE INVENTION

The present invention is more particularly described in the following examples which are intended as illustrative only since numerous modifications and variations therein will be apparent to those skilled in the art.

As used in the specification and in the claims, "a" can mean one or more, depending upon the context in which it is used. "SLF" and "SCF" are used interchangeably to refer to steel factor.

The invention provides a vector for targeted delivery of a nucleic acid to a cell comprising a biotinylated encapsidated virus, wherein the virus is linked via streptavidin to a biotinylated targeting moiety. The encapsidated virus can be recombinant and can comprise the nucleic acid to be delivered to the cell. The vector can be in a cell, either in vivo or in vitro.

The present vectors were generated by direct high affinity linkage of the targeting moiety to a recombinant adenovirus particle. To achieve these inventive vectors, we developed a protocol for the covalent addition of biotin to the capsid of recombinant adenovirus particles. We have demonstrated that biotin can be linked to the capsid of recombinant adenovirus while maintaining wild-type infectivity. Following incubation with streptavidin, any biotinylated ligand or antibody could be added to target this vector to any cell type. Following incubation of this vector with biotinylated SLF, up to a one thousand fold increase in luciferase gene expression was observed. Expression of the transferred gene was observed over 96 hours. Versatility of the vector of this invention was demonstrated by substituting targeting moieties: antibodies to four different cell surface markers for SLF, which resulted in targeted gene transfer to cell lines expressing those specific markers. Thus the present invention provides vectors and methods that can achieve targeted transient expression of nucleic acids, such as cytotoxic genes, tumor-specific ribonucleases and growth suppressor. These vectors can be utilized for therapeutic applications, such as treatment of leukemic cells, treatment of solid tumors in any cancer that expresses a tumor-specific cell surface marker, such as breast cancer, lung cancer, cervical cancer, pancreatic cancer, liver cancer, colon cancer, prostate cancer and melanoma. The invention can also be used to treat viral and bacterial infections and autoimmune diseases.

Thus, the present invention provides a composition for targeted delivery of a nucleic acid to a cell comprising a biotinylated recombinant encapsidated virus, wherein the recombinant virus comprises the nucleic acid, and wherein the biotinylated recombinant virus is linked via streptavidin to a biotinylated targeting moiety. The method can be used with small, encapsidated viruses. Examples of virus can include adenovirus and adeno-associated virus (AAV). Choice of viral vector can vary depending upon the purpose of the gene transfer. For example, for transient expression of the transferred gene, adenoviral vectors would be useful; for longer term expression, AAV vectors would be useful.

Thus, in one example, the present invention provides a composition for targeted delivery of a nucleic acid to a cell comprising a biotinylated recombinant adenovirus, wherein the recombinant adenovirus comprises the nucleic acid, and wherein the biotinylated recombinant adenovirus is linked via streptavidin to a biotinylated targeting moiety. The targeting moiety can be, for example, a ligand, an antibody, e.g., an antibody directed against cell surface markers for steel factor (such as anti-CD117 antibodies) or other antibodies (e.g., anti-CD34, anti-CD44, anti-CD45, anti-CD5, anti-CD3, anti-CD4, anti-CD8, and anti-LFA-1). The molecule on the cell targeted by the targeting moiety can be any selected targeted moiety, such as a cell surface receptor, such as a receptor that binds steel factor (c-kit). To target hematopoetic cells, for example, the receptor for steel factor (c-kit) can be targeted with an anti-c-kit antibody or it can be targeted with the steel factor itself linked by biotin-avidin-biotin to the virus with success at above of 99%. The antibodies, anti-CD45, anti-CD5, anti-CD3, anti-CD4, anti-CD8, and anti-LFA-1, are shown herein to be particularly effective at targeting primary T cells and NK cells. The vectors may be used for a variety of purposes, such as antisense delivery vectors, gene therapy vectors, and vaccines.

Steel factor can be soluble or membrane associated and is described in Godin et al. (Effects of the steel gene product on mouse primordial germ cells in culture, Nature 352, 807–809, 1991), Dolci et al. (Requirement for mast cell growth factor for primordial germ cell survival in culture, Nature 352, 809–811, 1991) and Matsui et al. (Effect of steel factor and leukemia inhibitory factor on murine primordial germ cells in culture, Nature 353, 750–752, 1991). Soluble steel fragment refers to a fragment cleaved from the extracellular domain at a specific proteolytic cleavage site. Membrane associated steel factor refers to both normal steel factor before it has been cleaved or the steel factor which has been altered so that proteolytic cleavage cannot take place. Steel factor is well known in the art; see European Patent Publication No. 0 423 980 A1, corresponding to European Application No. 90310889.1.

The vector can be used to transfect many types of cells. For example cell lines and primary cells have been targeted successfully by the present method. Examples of cell lines include, but are not limited to MO7e cells, cultured cells include, but are not limited to NK cells, and primary cells include, but are not limited to peripheral T cells and peripheralized stem cells. Peripheralized stem cells are stem cells that have been stimulated to leave the bone marrow and move into the blood, where they may be collected. In primary cells, the results using the biotinylated virus linked via avidin to biotinylated targeting moiety show a ten fold improvement in transfection over the control vector. Also, the favorable results with the NK cells is worthy of note, since NK cells are known to be very difficult to transfect. Having shown that the present vector is effective in a wide variety of cell types, the present invention has provided a vector that can be used in many different cell types. Although hematologic cells have been emphasized, the invention is by no means limited to just hematologic cells.

The present invention further provides a method for targeted delivery of a nucleic acid to a selected cell in a subject comprising administering to the subject a composition comprising a biotinylated recombinant adenovirus, wherein the recombinant adenovirus comprises the nucleic acid, wherein the virus is linked via streptavidin to a biotinylated targeting moiety that specifically targets the selected cell.

The subject can be any animal, preferably a mammal, such as a human, a veterinary animal, such as a cat, dog, horse, pig, goat, sheep, or cow, or a laboratory animal, such as a mouse, rat, rabbit, or guinea pig.

Any nucleic acid can be selected for use in the vector, and thus transferred into the target cell. For example, the GENBANK and EMBL databases can be searched to find genes/nucleic acid sequences desired to use in a vector. The nucleic acid transferred into a targeted cell by a vector of the present invention can be a nucleic acid that functionally encodes a protein or it can encode an oligonucleotide (e.g., antisense RNA, expression regulatory sequences). A nucleic acid encoding a selected protein can readily be determined based upon the amino acid sequence of the selected protein, and, clearly, many nucleic acids will encode any selected protein. The nucleic acid can comprise a sequence that promotes cell-type specific expression (Wirak et al., *EMBO* 10:289 (1991)). For example, to functionally encode, i.e., allow the nucleic acid to be expressed, the nucleic acid can include, for example, exogenous or endogenous expression control sequences, such as an origin of replication, a promoter, an enhancer, and necessary information processing sites, such as ribosome binding sites, RNA splice sites, polyadenylation sites, and transcriptional terminator sequences. Construction of such polynucleotides is well-known in the art and is described further in Maniatis et al., *Molecular Cloning: A Laboratory Manual,* 2nd Ed., Cold Spring Harbor Laboratory, Cold Spring Harbor, N.Y. (1989). Preferred expression control sequences can be promoters derived from metallothionine genes, actin genes, immunoglobulin genes, CMV, SV40, adenovirus, bovine papilloma virus, etc.

The promoter utilized can be any desired promoter, selected by known considerations, such as the desired level of expression of a nucleic acid functionally linked to the promoter and the cell type in which the vector is to be used. Promoters can be an exogenous or an endogenous promoter. Promoters can include, for example, known strong promoters such as SV40 or the inducible metallothionein promoter, or an AAV promoter, such as an AAV p5 promoter. Additional examples of promoters include promoters derived from actin genes, immunoglobulin genes, cytomegalovirus (CMV), adenovirus, bovine papilloma virus, adenoviral promoters, such as the adenoviral major late promoter, an inducible heat shock promoter, respiratory syncytial virus, Rous sarcomas virus (RSV), etc. To facilitate targeted expression of the nucleic acid in a particular tissue, a tissue specific promoter can be used in the vector. Examples of such promoters are known in the art.

The protein expressed by a cell transfected with the present invention can be isolated for use. The protein can be readily obtained by any of several means. The coding regions of the transfected genes can be expressed or synthesized, an antibody specific for the resulting polypeptide can be raised by standard methods (see, e.g., Harlow and Lane, *Antibodies: A Laboratory Manual,* Cold Spring Harbor Laboratory, Cold Spring Harbor, N.Y., 1988), and the protein can be isolated from other cellular proteins by selective interaction with the antibody. This protein can be purified to the extent desired by standard methods of protein purification (see, e.g., Sambrook et al., *Molecular Cloning: A Laboratory Manual,* 2nd Ed., Cold Spring Harbor Laboratory, Cold Spring Harbor, N.Y., 1989).

Nucleic acids can also include sequences encoding antisense oligonucleotides that can be transferred into cells to, upon expression, reduce or eliminate the expression of a gene, particularly associated with a disease or condition, typically by binding to mRNA encoded by the target gene. Nucleic acids can range in size, and will generally be from 10 to 6000 nucleotides in length. The preferred length will depend on the intended purpose of the nucleic acid and the viral vector; if to encode a protein or polypeptide, it will have a length determined by the number of amino acids to be encoded, and if to encode a antisense molecule, it will have a length chosen to allow or maximize hybridization to the target nucleic acid (typically, 10 to 40 nucleotides). If adenovirus is used, the nucleic acid can be up to about 35 kilobases (kb). If AAV-2 is used the nucleic acid is considerably small, in the range of about 4.3 kb. Oligonucleotides having the selected binding specificity can readily be determined, as known in the art. For general methods relating to antisense polynucleotides, see *Antisense RNA and DNA*, D. A. Melton, Ed., Cold Spring Harbor Laboratory, Cold Spring Harbor, N.Y. (1988).

The target can include a tissue, an organ, a cell, protein, a peptide, or uncharacterized markers and targets. For example, one can target cells of a tumor, metastatic cells, cells of the vasculature (such as endothelial cells and smooth muscle cells), cells of the lungs, muscle (such as smooth muscle cells, cardiac muscle, etc.), cells of the kidneys, blood cells (such as T-cells), cells of the bone marrow, such as stem cells, cells of bone, neurons and related neurological cells such as glial cells, brain cells, liver cells, or precursors of any selected cell, etc. by selecting a ligand, targeting motif or antibody specific for the tissue or cells, such as a targeting motif or domain that specifically binds a cell surface receptor expressed on the cells of the organ or tissue. The present vector can be targeted to the mucosa. For example the target receptor can be an integrin, such as $\alpha v \beta 3$, $\alpha v \beta 5$, $\alpha II \beta 3$, a growth factor receptor, a hormone receptor, a cytokine receptor, and the like. The target receptor can be a growth factor-dependent receptor (e.g., epidermal growth factor, nerve growth factor, etc.). The target receptor can also be a ligand-dependent receptor (such as a steroid receptor, thyroid hormone receptor, retinoic acid receptor, retinoid X receptor, TCCD (dioxin) receptor, fatty acid activatable receptors, and the like) or a stimulus-dependent receptor (such as peroxisome proliferator-activated receptor). Many of these receptors or factors can be found listed in Parker, M. G. (1993) *Steroid Hormone Action* (Oxford University Press, New York, pp. 210), in Tsai, M. J. & O'Malley, B. W. (1994) *Annu. Rev. Biochem.* 63, 451–486, and in the GenBank database, which will contain additional receptors as well as the complete nucleotide sequences of the genes and cDNAs. The targeting moiety is selected based on the cellular target, and it is routine to make such a selection.

Depending upon the target, the present invention can be used in treatment of various conditions and diseases, to increase expression of a desired protein, to inhibit expression or function of a gene product, etc. Any condition or disease in which transfer and expression of a gene would be beneficial, such as by reducing or eliminating symptoms of the disease or condition can be treated by this method. For example, one can treat leukemia, treat viral infections (e.g., HIV, HCV, HSV, HPV, hepatitis, influenza, etc.), reduce in size or eliminate or prevent metastasis of solid tumors that express a tumor-specific cell surface marker, such as melanoma, breast cancer, prostate and colon cancer among others. The vector of the invention can also be used to administer nucleic acids encoding vaccine antigens for presentation of antigen by the target cells.

Vectors of the invention can be administered to a subject or an animal (e.g., for veterinary use or in animal model testing) by any of many standard means for administering the a composition. The vectors can be administered orally, parenterally (e.g., intravenously), by intramuscular injection, by intraperitoneal injection, topically, transdermally, to the mucosa, or the like. Vector can also be delivered stereotactically for neural administration. Compositions can include various amounts of the selected vector in combination with a pharmaceutically acceptable carrier and, if desired, may include other medicinal agents, pharmaceutical agents, carriers, adjuvants, diluents, etc. Parental administration, if used, is generally characterized by injection. Injectables can be prepared in conventional forms, either as liquid solutions or suspensions, solid forms suitable for solution or suspension in liquid prior to injection, or as emulsions. Dosages will typically be in the range of, for example, for direct injection into a cell, tissue or organ, about $2 \times 10^7$–$2 \times 10^9$ infectious particles; for intraperitoneal administration, about $10^7$, $10^8$, $10^9$ or up to $10^{12}$ infectious particles; for inhalation into the airway, about $2 \times 10^9$ pfu in about a 20 ml volume; for direct instillation into the intrapleural space of the lung, about $1 \times 10^9$ pfu, which can escalate to about $1 \times 10^{11}$; for stereotactic administration into the CNS, about $10^8$–$10^{11}$ infectious particles; and can be a dosage that can achieve protein levels of the transfected gene, such as about 1–10 ng of reporter gene protein/mg cell protein, as shown herein for luciferase.

Furthermore, the present invention can be used to administer a vector into a cell ex vivo, such as for then transferring the cell into a subject. For example, one can transfect a cell, such as a blood cell, a liver cell, a kidney cell, a neuronal cell, etc., that has been removed from a subject and, after transfection, transplant the cell back into the patient. For example, one could harvest a subject's T cells, transfect them with a vector having an HIV antisense sequence, and return the cells to the patient to treat an HIV infection or to render the subject resistant to HIV invention. Alternatively, one can transfect cells derived from a donor subject or cultured cells and transplant the transfected cell into the subject.

In general, for such an ex vivo administration, cells are isolated from a subject by standard means according to the cell type and placed in appropriate culture medium, also according to cell type (see, e.g., ATCC catalog). The cells are then contacted with a vector as appropriate for the cell type, and the vector is allowed to transfer into the cells. Cells can then be transplanted back into the subject's body, by means standard for the cell type and tissue (e.g., in general, U.S. Pat. No. 5,399,346).

The present vectors can also be utilized to transfer a nucleic acid into a selected cell type in vitro. Such transfers can be utilized for a variety of purposes, such as to create a cell that can produce large quantities of a selected protein, which can then be harvested. The present vector and method can be particularly useful when the cell composition contains more than one cell type, and a specific cell present in the composition is to be targeted.

EXAMPLES

Production of Targeted Recombinant Viral Vectors

One example of the viral component of the vector is a recombinant human serotype 5 adenovirus (Ad5) which is replication deficient due to a deletion of the early 1 (E1) gene. Specifically, the gene for the enzyme firefly luciferase, under transcriptional control of the CMV promoter and with an SV40 polyA addition sequence, was introduced into the viral E1 coding region by homologous recombination (AdCMV-Luc). Replication defective AdCMV-Luc was propagated in the cell line 293, which carries the Ad5 E1 gene in its genome to compliment the deletion in AdCMV-Luc. Concentrated Adluc suspensions were produced by infecting 293 cells with the virus, allowing time for the virus to replicate, and purifying the virus from lysates of these cells. Specifically, adherent 293 cells were grown to approximately 80% confluency in T150 flasks in Minimum Essential Media (MEM) containing 10% FBS and Pen/Strep (complete MEM). The media was then replaced with 10 ml MEM containing 2% FBS and the cells were infected with Adluc at a multiplicity of infection (MOI) of between 0.1 and 1. Infected cells were incubated for 2 hours at 37° C. prior to adding 20 ml of complete MEM. Flasks were then incubated at 37° C. until the cells became rounded from cytopathic effects of the viral infection, generally about 48 hours. Cells were detached by gentle shaking and collected by centrifugation at 200 ×g at 4° C. for 10 minutes. The cells were lysed by 4 freeze/thaw cycles, the cellular debris pelleted by centrifugation at 3500×g at 4° C. for 20 minutes, and the supernatant containing the adenoviral particles was collected. This supernatant was concentrated and purified twice by ultracentrifugation over a discontinuous cesium chloride gradient of 1.33 and 1.45 mg/ml and the apparent lower band collected. Cesium chloride was removed by passing the suspension through a desalting column and the purified Adluc suspension was then used in the vector production or stored at −70° C. after a 1:1 dilution in viral preservation media (10 mM Tris pH 8.0, 50 mM NaCl, 0.1% BSA, 50% glycerol) was made.

Biotin was covalently linked to intact adenoviral particles using a protocol for photoactivatable biotinylation. Briefly, 7.0 ml of purified Adluc suspended in Hepes buffered saline (HBS), with a titer of $1.4 \times 10^{11}$ particles/ml, was treated in the dark with 100 μg/ml Immunopure photoactivatable biotin (~$8 \times 10^5$ biotins per virion), although as little a 25 μg/nl or a much as 1000 μg/ml can be used. Five hundred microliter aliquots of the virus/photoactivatable biotin mixture were placed on ice in open 1.0 ml Nunc tubes and the tubes irradiated at a wavelength of 350 nm for 5 minutes in a laminar flow hood. Exposure of the photoactivatable biotin to 350 nm light produces a reactive nitrine which then covalently links the biotin to any adjacent molecules. Although the reactive nitrine prefers to react with amino groups it is a non-specific binding process even capable of replacing C—H and C—C bonds. The suspension was then passed through a PD-10 column containing Sephadex G-25 (Pharmacia) to remove any unbound biotin and the effluent contained the biotinylated recombinant adenovirus (bio-Adluc). This process can use other types of biotin, however it should be noted that it is possible to overbiotinylate the virus to an extent that results in the formation of insoluble complexes when avidin is added. This phenomenon was not encountered at the above concentrations of biotin.

Attachment of a biotinylated ligand to biotinylated recombinant adenovirus requires the addition of an avidin bridge to link the virus to the ligand. To add the avidin bridge, 500 μl of bio-Adluc in viral preservation media, with a titer of $1 \times 10^{10}$ particles/ml, was incubated for 30 minutes at room temperature with 2.5 μg Neutravidin (Pierce) for a final concentration of 5 μg/ml (~$1 \times 10^4$ Neutravidin molecules/virion). Unbound Neutravidin was removed by gel filtration through a PD-10 column containing a 5 milliliter bed volume of Sephacryl 300 (S-300) equilibrated with HBS.

Recombinant AAV is substituted in the above method to produce an AAV-based vector of this invention. Biotynylated AAV-2 has thus been produced, as above, with the exception that a different column is used to purify the biotinylated virus. Likewise bitinylated retrovirus has also been made using the method described above, without significant reduction in infectivity.

Infection of Cells with Targeted Vector

The protocol for infecting MO7e cells with a SCF-targeted vector was as follows 1) A suspension of biotinylated recombinant adenovirus containing approximately $1 \times 10^{11}$ particles/ml in viral preservation buffer was treated with 5.0 μg/ml Neutravidin for 45 minutes at room temperature to produce biotinylated recombinant adenovirus linked to avidin (control vector) 2) Five hundred μl volumes were filtered through PD-10 columns containing a 5 ml bed of S-300 gel equilibrated with HBS to remove excess avidin 3) To make the SCF-targeted vector, biotinylated recombinant adenovirus linked to avidin was incubated with recombinant human bio-SCF at a concentration of 250 ng/ml for 30 minutes at room temperature 4) $1.5 \times 10^6$ MO7e cells in 1.0 ml RPMI 1640 containing 2% sera and 30 ng/ml GM-CSF (infection media) were treated with 100 μl of the SCF-targeted or a control vector to obtain an MOI of between 75 and 250 5) The virus/cell mixture was incubated in 6 well plates for two hours at 37° C., then diluted with 2.0 ml RPMI media to obtain a final concentration of 10% FBS, 100 ng/ml SCF, 30 ng/ml GM-CSF and IL-3 and incubated for 24 to 48 hours (or longer as indicated) at 37° C. To assay for luciferase activity, cells were collected, washed once with PBS and lysed with between 75 and 300 μl of lysis buffer containing 1% Triton-X 100, 50 mm NaCl, 10 mM Tris pH 7.6 and 5 mm EDTA.

NK cells, peripheral T cells and peripheralized stem cells are transfected by the present vector using the basic protocol described above.

Peripheralized Stem Cells: Peripheral blood (GM-CSF mobilized) were cryopreserved. We thawed them, separated the light density fraction on Ficoll gradients, and used these cells as targets for SCF directed, anti-CD34 and anti-CD44 directed infection. Using essentially the method as described for MO7e cells, targeting was successful with antiCD-44 vectors. Next, the cell population is enriched to target c-kit and CD44.

Primary T Cells: The cells were separated on Percoll gradient (yields>90% pure population of T-cells) and cultured 48 hours in absence (unstimulated) and presence (stimulated) of 1 μg/ml PHA. Using essentially the method as described for MO7e cell, the cells were used as targets for virus infection. Increases in infection of unstimulated cells was observed with anti-CD44 (anti-CD3 moderately). Cells were stimulated with bio IL-2, anti-CD4, anti-CD8, anti-CD44, anti-CD5, anti-CD45, and anti-LFA-1 α.

NK Cells: NK cell lines were used in an identical manner to that described for MO7e cells. MB02, KG1a, K562, HL-60 cell lines, etc. can also be transfected using the same basic protocol as described. Positive results were obtained for targeting with anti-CD45, anti-LFA1α, anti-CD44, bio IL-2.

Antibody-Targeted Vectors

To switch the specificity of vector targeting biotinylated, antibodies were substituted for the bio-SCF used in step 3 above. All other portions of the protocol were unchanged. Specifically, to target CD34 and CD117, biotinylated monoclonal antibodies to these antigens were used at 20 μg/ml and to target CD44 the antibody was used at 2.5 μg/ml.

Expression Assays

Luciferase assays were performed according to the protocol provided with reagents purchased from Promega. Briefly, 20 μl of cell lysate are mixed with 100 μl of luciferase assay reagent and the light emission, in relative light units, determined on a luminometer using a 10 second measuring time. Four consecutive 10 second measurements were made and the average emission calculated.

Protein assays were performed on lysates using a Pierce BCA protein assay. Briefly, 10 μl of the cell lysate is mixed with 200 μl of the BCA protein assay reagent, incubated for 30 minutes at 37° C. and the protein content determined by comparison to BSA standards following determination of the absorption of light at a wavelength of 595 nm on a spectrophotometer. Duplicate samples were evaluated and the average protein concentration calculated.

The luciferase activity in the cell lysate was determined by dividing the average emission determined on the luminometer by the average protein content in the sample to obtain a value reported as relative light units per milligram of protein (RLU/mg).

Targeting and Expression Results

Results are presented in FIGS. 1–10. As can be seen, transfection is specific and dependent upon the linkage of targeting moiety to the adenoviral vector.

In gene transfer to cell lines, experiments have been performed to assay the percentage of cells transfected by the present vectors that have luciferase gene as the transferred DNA. Transfected cells were fixed and assayed individually for presence of luciferase DNA. Greater than 95% of cells were positive for the presence of luciferase DNA. Additionally, untransfected cells were assayed for background; background was found to be essentially zero.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A composition comprising a biotinylated recombinant adenovirus that comprises a nucleic acid, wherein biotin is covalently linked to the recombinant adenovirus, and wherein the recombinant adenovirus is linked via streptavidin to a biotinylated targeting moiety.

2. The composition of claim 1, wherein the targeting moiety is a ligand.

3. The composition of claim 2, wherein the ligand is an antibody.

4. The composition of claim 1, wherein the targeting moiety is steel factor.

5. The composition of claim 1, wherein the targeting moiety is an antibody directed against cell surface markers for steel factor.

6. The composition of claim 1, wherein the targeting moiety is antibody anti-CD34.

7. The composition of claim 1, wherein the targeting moiety is antibody anti-CD44.

8. The composition of claim 1 wherein the targeting moiety is antibody anti-CD117.

9. The composition of claim 1, wherein the nucleic acid encodes a cytotoxic protein.

10. A composition comprising a biotinylated recombinant encapsidated virus that comprises a nucleic acid, wherein biotin is covalently linked to the recombinant virus, and wherein the recombinant virus is linked via streptavidin to a biotinylated targeting moiety.

11. The composition of claim 10, wherein the virus is an adenovirus.

12. The composition of claim 10, wherein the virus is an adeno-associated virus.

13. The composition of claim 10, wherein the targeting moiety is a ligand.

14. The composition of claim 10, wherein the targeting moiety is an antibody.

15. The composition of claim 10, wherein the targeting moiety is steel factor.

16. The composition of claim 10, wherein the targeting moiety is an antibody directed against cell surface markers for steel factor.

17. The composition of claim 10, wherein the targeting moiety is antibody anti-CD34.

18. The composition of claim 10, wherein the targeting moiety is antibody anti-CD44.

19. The composition of claim 10, wherein the targeting moiety is antibody anti-CD117.

20. The composition of claim 10, wherein the nucleic acid encodes a cytotoxic protein.

* * * * *